(12) United States Patent
Selcuk

(10) Patent No.: US 8,551,339 B2
(45) Date of Patent: Oct. 8, 2013

(54) USE OF SILICA FOR THE REMOVAL OF ORGANOSILANES

(75) Inventor: Sibel Selcuk, Westfield, IN (US)

(73) Assignee: Heritage Environmental Services LLC, Indianapolis, IN (US)

( * ) Notice: Subject to any disclaimer, the term of this patent is extended or adjusted under 35 U.S.C. 154(b) by 465 days.

(21) Appl. No.: 12/718,058

(22) Filed: Mar. 5, 2010

(65) Prior Publication Data
US 2010/0224568 A1 Sep. 9, 2010

Related U.S. Application Data

(60) Provisional application No. 61/158,059, filed on Mar. 6, 2009.

(51) Int. Cl.
 *C02F 1/42* (2006.01)
(52) U.S. Cl.
 USPC ........... 210/660; 210/662; 210/663; 210/690; 210/691; 210/767
(58) Field of Classification Search
 USPC .......... 210/660, 662, 663, 690–691, 751, 767
 See application file for complete search history.

(56) References Cited

U.S. PATENT DOCUMENTS

| | | | |
|---|---|---|---|
| 4,395,460 A | 7/1983 | Gaul | |
| 4,411,740 A * | 10/1983 | Flaningam et al. | 203/58 |
| 4,552,973 A | 11/1985 | Feldner et al. | |
| 4,745,205 A | 5/1988 | Haluska | |
| 4,885,378 A | 12/1989 | Band et al. | |
| 4,916,200 A | 4/1990 | Burns | |
| 5,290,342 A * | 3/1994 | Wikman et al. | 95/143 |
| 5,569,775 A * | 10/1996 | Diaz et al. | 556/466 |
| 6,211,345 B1 | 4/2001 | Weller et al. | |
| 6,350,797 B1 | 2/2002 | Weller | |
| 6,448,426 B1 | 9/2002 | Backer et al. | |
| 6,452,034 B2 | 9/2002 | Cruse | |
| 6,534,668 B2 | 3/2003 | Backer et al. | |
| 7,258,795 B1 * | 8/2007 | Nemeth et al. | 210/670 |
| 8,268,046 B2 * | 9/2012 | Watanabe et al. | 95/116 |
| 2008/0185333 A1 * | 8/2008 | Gibson et al. | 210/508 |

OTHER PUBLICATIONS

Herzog, U. et al., "Formation and characterization of cyclic and polycyclic silthianes containing Si—Si bonds", *Journal of Organometallic Chemistry*, vol. 602, 2000, pp. 193-207.

* cited by examiner

*Primary Examiner* — Chester Barry
(74) *Attorney, Agent, or Firm* — Brinks Hofer Gilson & Lione

(57) ABSTRACT

A method of removing organosilanes from a sample which involves contacting the sample with silica and allowing the organosilanes to couple to the surface of the silica. The silica can be provided as particles that are added to and mixed with the sample, or provided as a reactive filter media to which the sample is contacted.

19 Claims, 1 Drawing Sheet

USE OF SILICA FOR THE REMOVAL OF ORGANOSILANES

RELATED APPLICATION

This application is based upon U.S. provisional patent application Ser. No. 61/158,059, filed Mar. 6, 2009, to which priority is claimed under 35 U.S.C. §120 and of which the entire disclosure is hereby expressly incorporated by reference.

TECHNICAL FIELD

The present invention relates to organosilanes. More particularly, the present invention is directed to a method of removing organosilanes from various sources, including process streams, waste streams, recycling streams, and solutions.

BACKGROUND ART

Monomeric silicon chemicals are known as silanes. A silane structure and an analogous carbon-based structure are shown as follows:

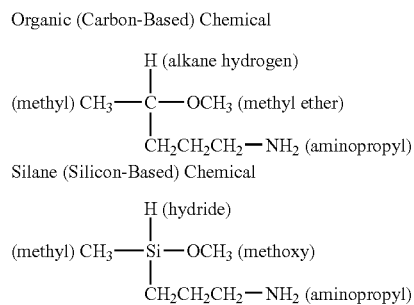

The four substituents above demonstrate differences and similarities in physical and chemical properties between silicon- and carbon-based chemicals. A silane that contains at least one carbon-silicon bond ($CH_3$—Si—) structure is known as an organosilane. The carbon-silicon bond is very stable, very non-polar and gives rise to low surface energy, non-polar, hydrophobic effects. Similar effects can be obtained from carbon-based compounds, although these effects are often enhanced with silanes. The silicon hydride (—Si—H) structure is very reactive. It reacts with water to yield reactive silanol (—Si—OH) species and, additionally, will add across carbon-carbon double bonds to form new carbon-silicon-based materials. The methoxy group on the carbon compound gives a stable methyl ether, while its attachment to silicon gives a very reactive and hydrolyzable methoxysilyl structure. The organofunctional group, the aminopropyl substituent, will act chemically the same in the organosilicon compound as it does in the carbon-based compound. The distance of the amine, or other organofunctional group, from silicon will determine whether the silicon atom affects the chemistry of the organofunctional group. If the organic spacer group is a propylene linkage (e.g., —$CH_2CH_2CH_2$—), then the organic reactivity in the organofunctional silane will be similar to organic analogs in carbon chemistry.

Certain reactive silanes, particularly vinyl silanes (—Si—CH=$CH_2$) and silicon hydrides (—Si—H), are useful reactive groups in silicon chemistry, even though the reactive group is attached directly to the silicon atom. Attachment of chlorine, nitrogen, methoxy, ethoxy or acetoxy directly to silicon yields chlorosilanes, silyl-amines (silazanes), alkoxysilanes and acyloxysilanes, respectively, are very reactive and exhibit unique inorganic reactivity. Such molecules will react readily with water, even moisture adsorbed on a surface, to form silanols. These silanols then can react with other silanols to form a siloxane bond (—Si—O—Si—), a very stable structure; or in the presence of metal hydroxyl groups on the surface of glass, minerals or metals, silanols will form very stable —Si—O-metal bonds to the surface. This is the key chemistry that allows silanes to function as valuable surface-treating and coupling agents. Chloro-, alkoxy-, and acetoxy-silanes and silazanes (—Si—NH—Si—) will react readily with an active hydrogen on any organic chemical (e.g., alcohol, carboxylic acid, amine, phenol or thiol) via a process called silylation:

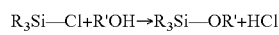

Silylation is very useful in organic synthesis to protect functional groups while other chemical manipulations are being performed. The silylated organofunctional group can be converted back to the original functional group once the chemical operation is completed. Silylation is very important in the manufacture of pharmaceutical products.

Silane coupling agents are silicon-based chemicals that contain two types of reactivity—inorganic and organic—in the same molecule. A typical general structure is:

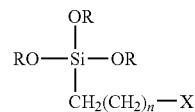

where RO is a hydrolyzable group, such as methoxy, ethoxy, or acetoxy, and X is an organofunctional group, such as amino, methacryloxy, epoxy, etc.

A silane coupling agent will act as an interface between an inorganic substrate (such as glass, metal or mineral) and an organic material (such as an organic polymer, coating or adhesive) to bond, or couple, the two dissimilar materials.

$R_nSi(OR)_{4-n}$ is the basic structure of organosilanes with "R" being an alkyl, aryl, or an organofunctional group and "OR" being a methoxy, ethoxy, or acetoxy group. Some examples of organosilanes include amino silanes, epoxysilanes, methacrylsilanes, phenylsilanes, alkylsilanes, chlorosilanes, vinylsilanes, sulfur substituted silanes etc.

The prevalent use and manufacture of organosilanes produces various process streams that contain organsilanes. In addition, depolymerization processes that are used to recover monomers from silicone containing materials, including silicone wastes, produce organosilane containing solutions.

The present invention is directed to a method for removing organosilanes from various sources, including process streams, waste streams, recycling streams and solutions.

DISCLOSURE OF THE INVENTION

According to various features, characteristics and embodiments of the present invention which will become apparent as the description thereof proceeds, the present invention provides a method of removing organosilanes from a sample which involves the steps of:

a) providing a sample containing organosilanes;
b) contacting the sample with silica; and c) allowing the organosilanes to couple to the surface of the silica.

BRIEF DESCRIPTION OF DRAWINGS

The present invention will be described with reference to the attached drawings which are given as non-limiting examples only, in which.

BEST MODE FOR CARRYING OUT THE INVENTION

The present invention is directed to a method for removing organosilanes from various sources, including but not limited to process streams, waste streams, recycling streams, and solutions. In process streams the present invention can prevent contamination of desired products by removal of undesirable organosilanes. Otherwise, more generally, the removal of organosilanes can be used for subsequent recovery of the organosilanes and/or cleanup treatment of various streams, solutions or sources.

Fumed silica, also know as silica fume, pyrogenic silica or colloidal silica can be utilized to remove organosilanes according to the present invention.

Conventional fumed silica is hydrophilic; having a surface covered with silanol (Si—OH) groups. The surface silanol groups provide for bonding with methoxy, ethoxy or the acetoxy groups hence making functionalized silica particles. The mechanism of using silica to remove organosilanes according to the present invention can generally be described by the following reaction in which silica is represented by the Si—O—Si—O chain structure:

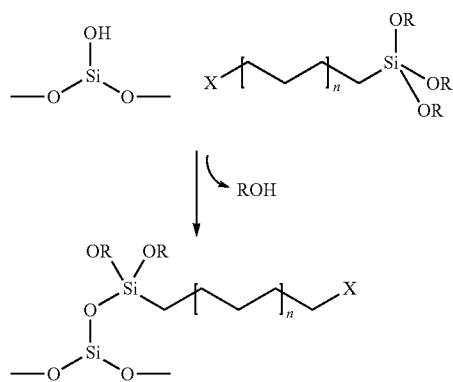

In this reaction one of the alkoxy groups of the illustrated organosilane $Si(OR)_3CH_2(CH_2CH_2CH_2)_nCH_2X$ reacts with the reactive silanol group (—Si—OH) on the surface of the silica. The resulting reaction couples the silica to the organosilane and releases the alcohol R—OH.

It is to be understood that in the illustrated organosilane $Si(OR)_3CH_2(CH_2CH_2CH_2)_nCH_2X$ both the carbon chain length and the X-functional group can change. In addition, the alkoxy groups could be hydroxyl, methoxy, ethoxy or acetoxy.

Since the coupling reaction of the organosilanes to the silica takes place at the silanol groups on the surface of the silica, the silica can be any convenient shape including particles of any shape, such as spherical particles, or structural shapes such as wafers, plates, etc, that can be incorporated into structural filters of filter assemblies, filter beds, fluidized beds, etc.

The fumed silica can be used as a reactive filter media in some cases to remove organosilane molecules, however; effective removal can also be obtained when silica is added to a sample containing organosilanes and mixed within the sample. Medium heat alone or heat together with reflux has been found to assist in the coupling of the organosilanes to the silica when necessary. If a sample begins to thicken a solvent such as methanol or ethanol can be added to the reaction media.

Figure 1:
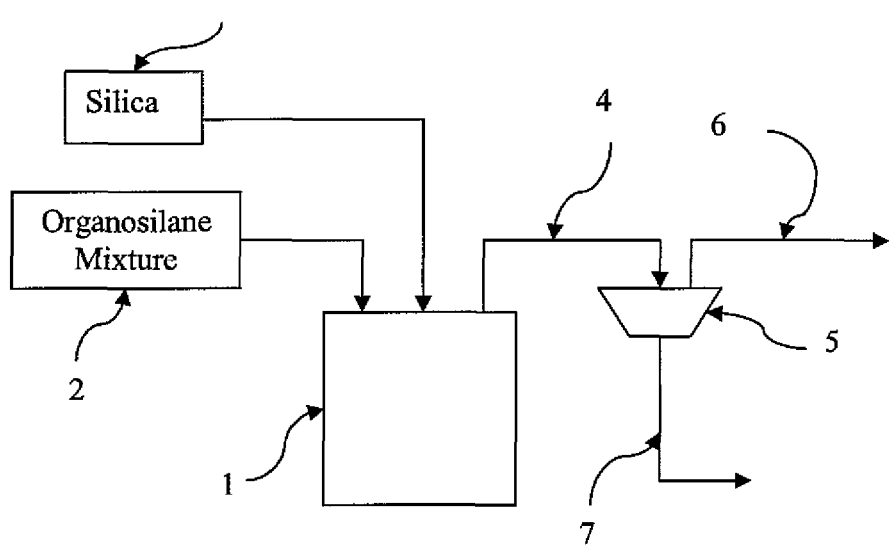
FIG. 1 is a process diagram according to one embodiment of the present invention.

FIG. 1 is a process diagram according to one embodiment of the present invention. As shown in FIG. 1 a reaction vessel 1 receives a sample 2 that contains organosilanes. The sample can be a liquid sample, a semi-liquid or solid (which is subsequently melted and/or dissolved and/or decomposed in reaction vessel 1). In the process depicted in FIG. 1, silica 3 is fed into reaction vessel 1 and mixed together in sample 2. The silica can be in any convenient shape, including spherical particles, or particles of any shape, including uniform or non-uniform shapes. The organosilanes from the sample mixture couple to the silica as discussed above. The reaction mixture can be heated during the reaction when needed. The temperature can range up to a temperature sufficient to create reflux of the mixture if desired. Generally temperatures of from about 40-80° C. are suitable. In the case of solid samples such as silicone containing materials (that are subject to depolymerization), the sample is heated to a temperature sufficient to melt the sample. During the reaction if the sample mixture begins to thicken or if the initial sample is viscous a solvent such as methanol or ethanol can be added to the reaction media.

After the organosilane-silica coupling reaction has reached a desired completion, the silica having the organosilanes coupled thereto can be recovered by sending the reactant mixture 4 to a separation device 5 which can be a filter, centrifuge, etc. which separates the solid silica (with the organosilanes coupled thereto) from the reaction mixture 4. The silica (with the organosilanes coupled thereto) 6 is recovered and the liquid phase 7 of the reactant mixture 4 can be recovered, reused and/or recycled. The organosilanes coupled to the silica can further processed and/or recycled.

Figure 2:
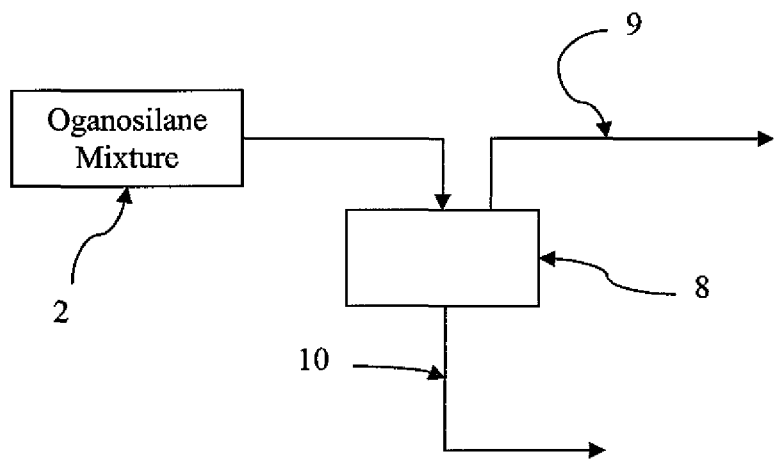
FIG. 2 is a process diagram according to another embodiment of the present invention.

FIG. 2 is a process diagram according to another embodiment of the present invention. In the embodiment of the invention depicted in FIG. 2 the silica is provided as a filter media or in a filter assembly generally identified by reference numeral 8 (and referred to herein as "filter 8"). In this embodiment the sample 2 that contains organosilanes is fed into filter 8. As the sample 2 passes through the filter 8, the organosilanes react with the silica and become coupled to the silica. The liquid phase 10 of the sample 2 (with some or all the organosilanes removed) is shown as leaving filter 8. The silica with the organosilanes coupled therefore can be removed from filter 8 as shown at 9. Otherwise, the organosilanes could be removed/uncoupled from the silica filter media or filter assembly chemically as exit stream 9.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

The following examples demonstrate the ability to remove organosilanes from a waste stream sample at room temperature according to the present invention.

Example 1

In this example Sample 1 (see Table 1 below) was prepared by mixing 30.7 grams of a waste stream with 30.2 grams of methanol. To this mixture 1.09 grams fumed silica is added and the resulting mixture was stirred for 60 hours at room temperature. A sample of the liquid waste stream was collected by filtration and tested for the presence of amino silanes. The initial weight percent of the amino silanes in the waste stream and final weight percents in the processed sample are presented in Table 1 below.

Example 2

In this example, a second test sample (Sample 2) was prepared in the same manner as Sample 1 above except that the mixture is stirred for 84 hours before obtaining the sample by filtration.

Example 3

In this example, another sample (Sample 3) was prepared in the same manner as Sample 1 except the mixture is stirred for 12 hours before obtaining the sample by filtration.

Example 4

In this example, an additional sample (Sample 4) was prepared as a control study to represent any amino silane mixture. This additional sample was prepared by spiking 29.8 gram of methanol with 1.6 grams of [3-(2-aminoethyl)aminopropyl]trimethoxysilane (AE-APTS) and 0.77 grams of N-(aminoethylamino)-3-isobutyldi-methylmethoxysilane (AE-AIBDS). To this mixture 1.06 gram fumed silica was added and the resulting mixture was stirred for 12 hours at room temperature before filtration. The initial and final weight percentages of the amino silane for all the above samples are presented in Table 1 below.

TABLE 1

| Example ID | AE-APTS | | AE-AIBDS | |
| --- | --- | --- | --- | --- |
| | Initial Weight % | Final Weight % | Initial Weight % | Final Weight % |
| Sample 1 | 5.58 | <0.1 | 1.16 | <0.1 |
| Sample 2 | 5.58 | <0.1 | 1.16 | <0.1 |
| Sample 3 | 5.58 | <0.1 | 1.16 | <0.1 |
| Sample 4 | 7.72 | 1.79 | 3.08 | 1.24 |

As can be seen from the results of Examples 1-4 in Table 1, silica can effectively remove organosilanes from organosilane-containing waste streams.

Although the present invention has been described with reference to particular means, materials and embodiments, from the foregoing description, one skilled in the art can easily ascertain the essential characteristics of the present invention and various changes and modifications can be made to adapt the various uses and characteristics without departing from the spirit and scope of the present invention as described above and set forth in the attached claims.

What is claimed is:

1. A method of removing organosilanes from a sample which comprises the steps of:
   a) providing a sample containing organosilanes and determining from the sample the amount of organosilanes in the sample;
   b) contacting the sample with silica by adding silica into the sample; and
   c) allowing the organosilanes to couple to the surface of the silica
   wherein in step b) a sufficient amount of silica is added into the sample based upon the determined amount of organosilanes in step a) to enable substantially all the organosilanes to couple to the surface of the silica.

2. A method of removing organosilanes from a sample according to claim 1, further comprising a step d) of removing from the sample the silica with surface coupled organosilanes after step c).

3. A method of removing organosilanes from a sample according to claim 1, wherein in step b) the silica is provided as a reactive filter media and the sample is contacted with the filter media.

4. A method of removing organosilanes from a sample according to claim 1, wherein the sample comprises a liquid.

5. A method of removing organosilanes from a sample which comprises the steps of:
   a) providing a sample containing organosilanes;
   b) contacting the sample with silica; and
   c) allowing the organosilanes to couple to the surface of the silica,
   wherein the sample comprises a solid which is dissolved or melted.

6. A method of removing organosilanes from a sample which comprises the steps of:
   a) providing a sample containing organosilanes;
   b) contacting the sample with silica; and
   c) allowing the organosilanes to couple to the surface of the silica,
   wherein the sample comprises a depolymerization reaction mixture.

7. A method of removing organosilanes from a sample which comprises the steps of:
   a) providing a sample containing organosilanes;
   b) contacting the sample with silica; and
   c) allowing the organosilanes to couple to the surface of the silica,
   wherein the sample comprises a process stream and the organosilanes that are removed are contaminants.

8. A method of removing organosilanes from a sample which comprises the steps of:
   a) providing a sample containing organosilanes;
   b) contacting the sample with silica; and
   c) allowing the organosilanes to couple to the surface of the silica,
   wherein the silica comprises fumed silica, pyrogenic silica or colloidal silica.

9. A method of removing organosilanes from a sample according to claim 1, further comprising heating the sample in any of steps a)-c).

10. A method of removing organosilanes from a sample according to claim 1, further comprising adding a solvent to the sample in any of steps a)-c).

11. A method of removing organosilanes from a sample according to claim 10, wherein the solvent comprises methanol or ethanol.

12. A method of removing organosilanes from a sample according to claim 5, further comprising a step d) of removing from the sample the silica with surface coupled organosilanes after step c).

13. A method of removing organosilanes from a sample according to claim 6, further comprising a step d) of removing from the sample the silica with surface coupled organosilanes after step c).

14. A method of removing organosilanes from a sample according to claim 7, further comprising a step d) of removing from the sample the silica with surface coupled organosilanes after step c).

15. A method of removing organosilanes from a sample according to claim 8, further comprising a step d) of removing from the sample the silica with surface coupled organosilanes after step c).

16. A method of removing organosilanes from a sample according to claim 5, wherein in step b) the silica is provided as a reactive filter media and the sample is contacted with the filter media.

17. A method of removing organosilanes from a sample according to claim 6, wherein in step b) the silica is provided as a reactive filter media and the sample is contacted with the filter media.

18. A method of removing organosilanes from a sample according to claim 7, wherein in step b) the silica is provided as a reactive filter media and the sample is contacted with the filter media.

19. A method of removing organosilanes from a sample according to claim 8, wherein in step b) the silica is provided as a reactive filter media and the sample is contacted with the filter media.

* * * * *